United States Patent [19]
Rivera et al.

[11] Patent Number: 5,609,885
[45] Date of Patent: Mar. 11, 1997

[54] OSMOTIC MEMBRANE AND DELIVERY DEVICE

[75] Inventors: David L. Rivera, San Jose; Sonya Merrill, Redwood City; James B. Eckenhoff; Jeremy C. Wright, both of Los Altos; James L. Osborne, Mountain View, all of Calif.

[73] Assignee: ALZA Corporation, Palo Alto, Calif.

[21] Appl. No.: 387,967

[22] Filed: Feb. 10, 1995

Related U.S. Application Data

[63] Continuation of Ser. No. 945,082, Sep. 15, 1992, abandoned.

[51] Int. Cl.$^6$ ........................................ A61K 9/24
[52] U.S. Cl. ........................ 424/473; 424/488; 604/892.1
[58] Field of Search ............................. 424/473, 488; 604/892.1

[56] References Cited

U.S. PATENT DOCUMENTS

| | | | |
|---|---|---|---|
| 4,595,583 | 6/1986 | Eckenhoff et al. | 424/15 |
| 4,612,186 | 9/1986 | Eckenhoff et al. | 424/15 |
| 4,624,945 | 11/1986 | Eckenhoff et al. | 514/30 |
| 4,663,148 | 5/1987 | Eckenhoff et al. | 424/454 |
| 4,663,149 | 5/1987 | Eckenhoff et al. | 424/452 |
| 4,675,174 | 6/1987 | Eckenhoff | 424/15 |
| 4,678,467 | 7/1987 | Eckenhoff et al. | 604/892 |
| 4,684,524 | 8/1987 | Eckenhoff et al. | 424/469 |
| 4,692,336 | 9/1987 | Eckenhoff et al. | 424/468 |
| 4,704,118 | 11/1987 | Eckenhoff | 604/892 |
| 4,716,031 | 12/1987 | Eckenhoff et al. | 424/453 |
| 4,717,566 | 1/1988 | Eckenhoff et al. | 424/438 |
| 4,717,568 | 1/1988 | Eckenhoff et al. | 424/469 |
| 4,717,718 | 1/1988 | Eckenhoff et al. | 514/30 |
| 4,729,793 | 3/1988 | Eckenhoff et al. | 106/169 |
| 4,731,122 | 3/1988 | Cortese et al. | 106/198 |
| 4,772,474 | 9/1988 | Eckenhoff et al. | 424/465 |
| 4,781,714 | 11/1988 | Eckenhoff et al. | 604/890.1 |
| 4,800,056 | 1/1989 | Eckenhoff et al. | 264/129 |
| 4,814,180 | 3/1989 | Eckenhoff et al. | 424/473 |
| 4,844,984 | 7/1989 | Eckenhoff et al. | 424/438 |
| 4,927,633 | 5/1990 | Eckenhoff et al. | 424/438 |
| 5,000,957 | 3/1991 | Eckenhoff et al. | 424/438 |
| 5,122,128 | 6/1992 | Cardinal et al. | 604/890.1 |

*Primary Examiner*—D. Gabrielle Phelan
*Attorney, Agent, or Firm*—Mary Ann Dillahunty; Steven F. Stone

[57] ABSTRACT

The present invention relates to an improvement in an osmotic delivery device wherein the device comprises a semipermeable wall comprising cellulose acetate butyrate and surrounding an internal compartment containing a beneficial agent or medicament formulation, a fluid-activated expandable driving member, optionally a partition layer between the agent formulation and the driving member, and, optionally a density member, and exit means in the semipermeable wall; and wherein the improvement comprises the cellulose acetate butyrate component of the semipermeable wall having a differential scanning calorimetry ("DSC") profile wherein the main or primary DSC peak has a minimum temperature peak above 228° C. and the secondary DSC peak area is equal to or less than about 30% of the total combined areas of the primary and secondary DSC peaks. The invention also relates to the improved semipermeable membrane produced from cellulose acetate butyrate having a differential scanning calorimetry ("DSC") profile wherein the main DSC peak is at a temperature above 228° C. and the secondary DSC peak area is equal to or less than about 30% of the total combined area of the primary and secondary DSC peaks, the semipermeable membrane providing a substantially improved uniform rapid startup performance for osmotic delivery devices.

8 Claims, 5 Drawing Sheets

OSMOTIC MEMBRANE AND DELIVERY DEVICE

This application is a continuation of application Ser. No. 07/945,082, filed Sep. 15, 1992, abandoned and benefit of the filing date of said earlier filed application is claimed under 35 U.S.C. §120.

FIELD OF THE INVENTION

This invention pertains to both a novel and a useful osmotic controlled release delivery device.

BACKGROUND OF THE INVENTION

Delivery systems for dispensing a beneficial agent to a biological environment of use are known to the prior art. For example, delivery devices having a fluid-permeable (semipermeable) membrane wall, an osmotically active expandable driving member and a density element for delivering a thermo-responsive beneficial agent formulation are known and are disclosed in, for example, U.S. Pat. Nos. 4,595,583; 4,612,186; 4,624,945; 4,663,148; 4,663,149; 4,675,174; 4,678,467; 4,684,524; 4,692,336; 4,704,118; 4,716,031; 4,717,566; 4,717,568; 4,717,718; 4,772,474; 4,781,714; 4,800,056; 4,814,180; 4,844,984; and 5,000,957. These dispensing devices of the prior art are extraordinarily effective for delivering beneficial agents that are hydrophilic, hydrophobic, lipophilic or lipophobic to a biological environment of use. The delivery devices operate successfully for their intended use, and they can deliver numerous difficult-to-deliver beneficial agents at a controlled and predictable rate.

However, the delivery devices, when placed into a biological environment of use, exhibit a delay to steady-state pumping or, in other words, they exhibit a startup period. One method of overcoming this startup delay is to prehydrate the device. Prehydration was found to be effective for initial test batches of the devices, producing uniform rapid startup of delivery of the beneficial agent when the devices were placed in the environment of use. But when prepared in larger-scale production lots, the devices exhibited inconsistent and much less uniform startup profiles when prehydrated with a constant volume of prehydration fluid, with many devices having an unacceptable delay before reaching steady-state pumping.

Therefore, those skilled in the art will appreciate that the development of improved delivery devices that will consistently exhibit a desired rapid startup behavior would be greatly desired and would be an advancement in the drug delivery art.

SUMMARY OF THE INVENTION

It has now been found by the inventors that the unacceptably slow and erratic delays in startup of the prior art devices occurred when the semipermeable membrane wall of the devices was manufactured using different commercial lots of cellulose acetate butyrate ("CAB"), a major component of the wall material. Commercial CAB is in the form of fibers and/or flakes and is available from Eastman Chemical Products. Although all lots of CAB fell within particular percentage ranges of butyryl and acetyl content, it has unexpectedly been found that very small changes in the acetyl, butyryl and hydroxyl content of the membrane composition have a surprisingly large influence on the properties of the semipermeable membrane with respect to the startup period. It has also been found that CAB membrane material exhibiting acceptable startup characteristics can readily be determined by the differential scanning calorimetry ("DSC") profile of the material.

The present invention relates to an improvement in an osmotic delivery device wherein the device comprises a semipermeable wall comprising in at least a part cellulose acetate butyrate and surrounding an internal compartment containing a beneficial agent or medicament formulation, a fluid-activated expandable driving member, optionally a partition layer between the agent formulation and the driving member, and, optionally a density element, and exit means in the semipermeable wall; and wherein the improvement comprises the cellulose acetate butyrate component of the semipermeable wall having a differential scanning calorimetry ("DSC") profile wherein the main or primary DSC peak has a minimum temperature peak above 228° C. and the secondary DSC peak area is equal to or less than about 30% of the total combined areas of the primary and secondary DSC peaks.

It has been found that CAB material exhibiting a DSC profile as described above generally has a butyryl content of less than 18.0%, an acetyl content of greater than 29.3%, and a hydroxyl content of less than 1.0%. These values, however, can vary somewhat, such as for example the acetyl content may be as low as at least 29.1% or the butyryl content may be as high as at least 18.2%, as long as the material has the DSC profile described above.

The invention also relates to the improved semipermeable membrane produced from cellulose acetate butyrate having a differential scanning calorimetry ("DSC") profile wherein the main DSC peak is at a temperature above 228° C. and the secondary DSC peak area is equal to or less than about 30% of the total combined area of the primary and secondary DSC peaks, the semipermeable membrane providing a substantially improved uniform rapid startup performance for osmotic delivery devices.

The present invention further pertains to a method for providing a consistent rapid startup of a prehydrated osmotic delivery device, the method comprising (a) prehydrating an osmotic delivery device, the delivery device comprising a semipermeable wall comprising in at least a part cellulose acetate butyrate and surrounding an internal compartment containing a beneficial agent or medicament formulation, an expandable driving member, optionally a partition layer between the agent formulation and the driving member, and, optionally a density member, and exit means in the wall, and wherein the cellulose acetate butyrate component of the semipermeable wall has a differential scanning calorimetry ("DSC") profile wherein the main DSC peak has a minimum temperature peak above 228° C. and the secondary DSC peak area is equal to or less than about 30% of the total prehydrated osmotic delivery device into an environment of use.

DETAILED DESCRIPTION OF THE INVENTION

Figure 1:
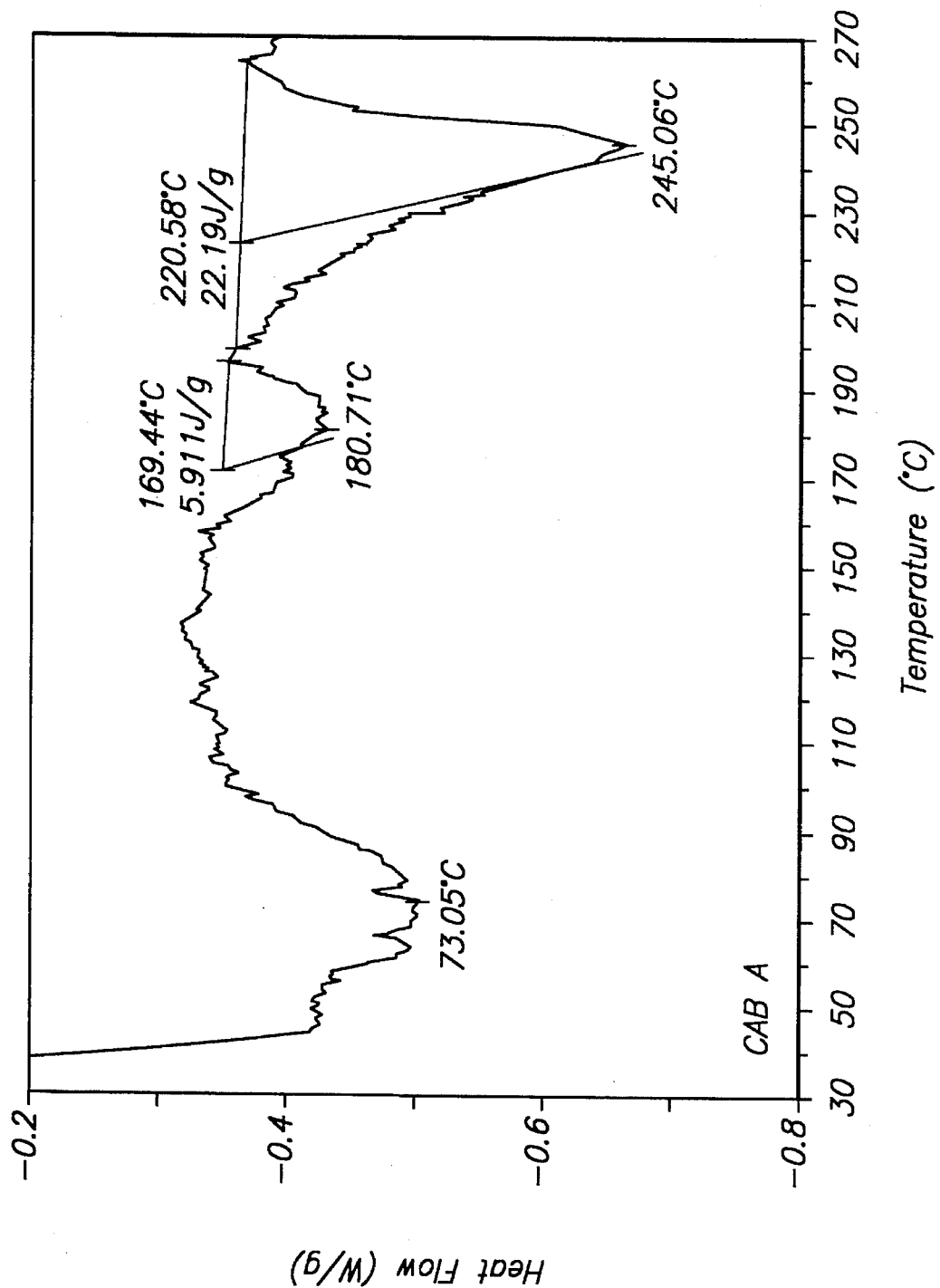
FIG. 1 shows a DSC profile for cellulose acetate butyrate (CAB) lot no. B17176 (Eastman Chemical) ("CAB A").

Semipermeable membranes useful in osmotic delivery devices may be made from a variety of polymers, such as are disclosed in the prior art. One particularly useful polymer is cellulose acetate butyrate. It was, found that cellulose acetate butyrate ("CAB") grade no. 171-15S (Eastman Chemical Products) often provided semipermeable membrane walls that were suitable for use in osmotic delivery devices, i.e. they provided acceptable startup. The published specification provided by Eastman for CAB 171-15S is 16.5–19.0% butyryl and 28.0–31.0% acetyl. However, within this one grade of CAB, while many of the lots within this grade and having these supposedly acceptable ranges provided acceptable startup, other of the lots did not. Analysis of the lots of CAB, both those that were acceptable for use in osmotic device membrane cups and those that produced unacceptable membrane cups, indicated that, generally, CAB providing acceptable startup has a butyryl content of less than 18.0%, an acetyl content of greater than 29.3%, and a hydroxyl content of less than 1.0%. However, this was not always the case, as can be seen in TABLE A. For example, CAB lot no. B18587 performed acceptably when tested for startup characteristics, even though lot B18587 has an acetyl content of 29.1% and a butyryl content of 18.2%.

the environment to the time of reaching a steady-state pumping rate.

Surprisingly, it was found that differential scanning calorimetry (DSC) profiles of CAB material provided a more reliable analytical measurement of CAB to give membrane cups with an acceptable startup performance. More particularly, it was found that acceptable CAB has a DSC profile wherein the main DSC peak is at a temperature above 228° C. and the secondary DSC peak area is equal to or less than about 30% of the total combined areas of the primary and secondary DSC peaks.

DSC measures endothermic phenomena. Without being bound by theory, it is believed that, in the case of CAB, there is a molecular orientation in the material, and the DSC peaks appear at the temperature (s) of reorientation. With CAB, the DSC profile generally contains three endothermic peaks. The first is a broad endotherm centered below 100° C. This endotherm may represent interaction of the CAB polymer with sorbed water. This first endotherm is not relevant to the evaluation of acceptable CAB under the present invention. The second endotherm, also referred to herein as the "secondary DSC peak", typically has a minimum temperature peak at about 180° C. to 195° C. The third endotherm, also referred to herein as the "primary DSC peak", typically has a minimum temperature peak at about 220° C. to 250° C. Acceptable, or "good", CAB is most easily distinguished from unacceptable, or "bad", CAB by the observation that the area of the second endotherm (secondary DSC peak) is much smaller than the area of the third endotherm (primary DSC peak) in good material, while the area of the second endotherm is about the same magnitude as the area of the

TABLE A

| EASTMAN LOT NO. | ACETYL CONTENT | BUTYRYL CONTENT | HYDROXYL CONTENT | STARTUP TEST | MAIN DSC PEAK | SECONDARY PEAK AREA |
| --- | --- | --- | --- | --- | --- | --- |
| B17636 | 29.9% | 17.5% | 0.75% | Acceptable | —# | —# |
| B17176 | 29.9% 30.0%* | 17.5% 16.8%* | 0.70% | Acceptable | 245° C. | 21% |
| B17085 | 28.7% 28.9%* | 18.1% 16.9%* | 1.11% | Poor | 213° C. | 47% |
| B18487 | 29.4% 28.9%* | 18.0% 17.4%* | 1.27% 1.11%* | Poor | 226° C. | 45% |
| B18447 | 29.7% 29.2%* | 17.0% 16.7%* | 0.96% 1.00%* | Acceptable | 229° C. | 21% |
| B18490 | 29.3% | 17.6% | 1.20% | Poor | 226° C. | 42% |
| B18587 | 29.1% | 18.2% | 0.80% | Acceptable | 234° C. | 24% |
| B18787 | 29.5% | 18.0% | 0.80% | Acceptable | 232° C. | 24% |
| B18788 | 29.5% | 18.0% | 0.80% | Acceptable | 230° C. | 29% |

*denotes a second analysis
not tested

The term "acceptable startup" characteristics or performance as used herein refers to membrane cups made from CAB which provide osmotic delivery devices with a consistent or uniform rapid startup to steady-state pumping when placed into an environment of use. In other words, substantially all of the devices have a minimum delay to steady-state pumping.

By "minimum delay" is meant a delay of no more than about 10 days, preferably of no more than about 7 days, and more preferably of no more than about 3 days from placement in the environment of use to the time of reaching a steady-state pumping rate when the devices are prehydrated. When the devices are anhydrous, that is they are not prehydrated prior to placement in the environment of use, the "minimum delay" is a delay of no more than about 21 days, preferably of no more than about 14 days, and more preferably of no more than about 10 days from placement in third endotherm in bad material. Measurement of the area of the peaks resulted in the observation that the area of the secondary peak in acceptable CAB contains less than about 30% of the total combined areas of the secondary and primary peaks. Additionally, the main DSC peak is above 228° C. in all lots of good CAB tested, while it is below 229° C. in all bad lots. Where the main peak is around 228° C., the controlling factor in determining whether the CAB is good or bad is whether the area of the secondary peak is less than 30% of the total areas.

Figure 2:
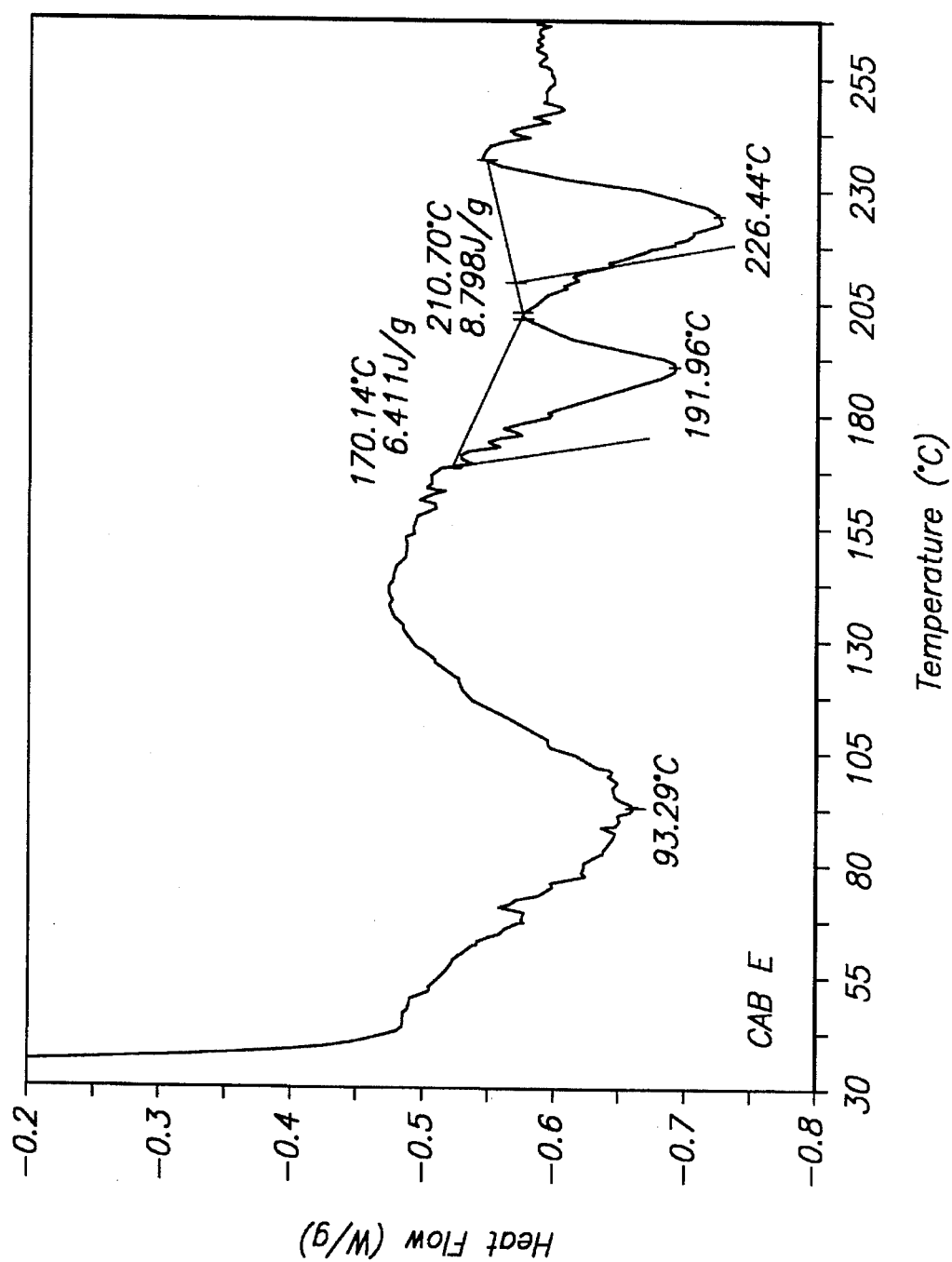
FIG. 2 shows a DSC profile for CAB lot no. B18490 (Eastman Chemical) ("CAB E").
Figure 3:
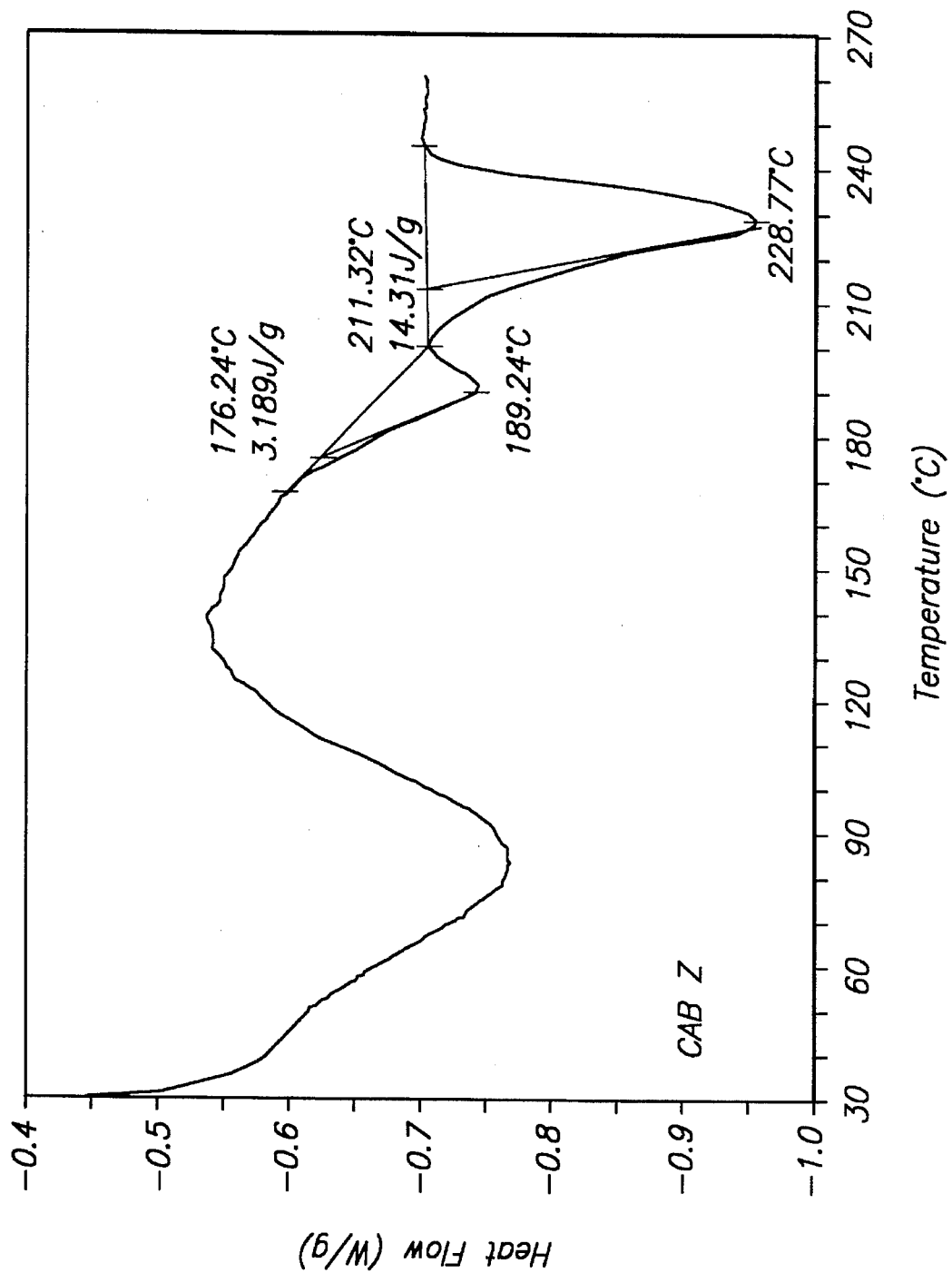
FIG. 3 shows a DSC profile for CAB lot no. B18447 (Eastman Chemical) ("CAB Z").

This is illustrated in FIGS. 1, 2 and 3. FIG. 1 shows a DSC profile for CAB lot no. B17176 ("CAB A"), which has been found to be "good" CAB when tested for uniform and rapid startup characteristics (see FIG. 4). The main DSC peak for this good CAB is at 245° C. and the secondary peak area is 21% of the total. In contrast, FIG. 2 shows a DSC profile of CAB lot no. B18490 ("CAB E"), which has been found to be "bad" CAB (see FIG. 4) in terms of startup characteristics, and has a main DSC peak at 226° C. and a secondary peak area of 42% of the total. FIG. 3 shows a DSC profile for CAB lot no. B18447 ("CAB Z"), which has a hydroxyl content of 0.96–1.0% and thus would have been considered to be borderline and possibly unacceptable if the hydroxyl content alone is looked at. However, when tested for its startup characteristics, it was found to be "good" CAB (see FIGS. 4 and 5); that is, while its startup was not as early as that of CAB A, it was within the acceptable range. A review of the DSC profile supports this finding, with this CAB Z having a main DSC peak at 229° C. and a secondary peak area of only 21% of the total.

Some CAB lots produce a small step change in their DSC scan at about 150° C. The measured area of the secondary peak may vary significantly depending on whether this step is or is not included in the area analysis. This step is excluded from the analysis in the practice of the present invention in determining the area of the secondary peak and the total area of the secondary and main peaks.

In determining the DSC profile for a particular CAB, a CAB sample is first prepared for the DSC scan by placing a small quantity, typically less than about 10 mg, of CAB into a standard crimp-style sample pan and crimping the lid on the pan over the sample. The sample is then placed at the proper location inside the DSC cell, with the temperature of the cell initially at room temperature. The instrument is programmed to equilibrate the sample at 30° C. and then to heat the sample to 270° C. at 20° C. per minute. An example of a DSC instrument which may be used is the DuPont Thermal Analyzer 2100. Examples of the data acquired during the heating segment are presented in FIGS. 1, 2 and 3.

The cellulose acetate butyrate according to the present invention is particularly useful for preparing semipermeable membranes for use in osmotic delivery devices for administering active agents such as drugs to an animal. Semipermeable membranes can be prepared by methods well known in the art, such as has been described in U.S. Pat. Nos. 4,729,793, 4,731,122, and those patents listed previously herein. Generally, the membrane is prepared by first granulating or comminuting the commercial fibers or flakes of CAB to obtain a small uniform particle size and then optionally blending with other semipermeable polymers if desired, such other polymers being known in the art. Additional excipients such as flux regulating agents and plasticizers, as are known in the art, may also be added to the CAB and any other polymer, and the blend is then either melted and molded to the desired shape, such as by injection molding, extrusion and the like, or is solubilized in a suitable solvent and sprayed or dipped or otherwise coated onto a capsule, a pill or other form of delivery device.

In a presently preferred embodiment, semipermeable membrane cups having a composition as presented under TABLE B are prepared as follows.

TABLE B

| Component | Range |
|---|---|
| CAB 171-15S | 48.0–50.5% |
| Cellulose Acetate | 16.5–18.0% |
| Triethyl citrate | 5.0–8.0% |
| Tributyl citrate | 21.0–23.0% |
| Polyethylene glycol 400 | 3.5–4.5% |
| Titanium dioxide | 0–1.25% |

Cellulose acetate is a semipermeable polymer. Suitable cellulose acetates for use in osmotic device semipermeable membranes are known in the art and are disclosed in, for example, the U.S. patents cited above. Triethyl citrate (Citroflex-2®, Morflex Inc.), tributyl citrate (Citroflex-4®, Morflex Inc) and polyethylene glycol with a molecular weight of 400 (PEG 400, Union Carbide) are plasticizers.

To process the raw materials for the cup, the cellulose acetate butyrate (CAB) is sized using suitable comminuting or granulating equipment. If titanium dioxide is included in the formulation, it is deagglomerated using a sieve or a suitable machine such as a comminuting machine. The CAB is added to a mixer, after which the plasticizer solution (containing tributyl citrate, triethyl citrate and polyethylene glycol 400) is added, with mixing. The cellulose acetate is added and the contents are blended together, after which the titanium dioxide is added, with blending. To prepare the membrane cups, the plasticizer/polymer blend is molded by means of injection molding. The blended polymers with plasticizers are melted and conveyed in molten form to an injection mold of the appropriate dimensions. The resulting semipermeable membrane cups are useful in osmotic delivery devices.

Osmotic delivery devices which exhibit a consistent and rapid startup are provided by the present invention. Such devices have a minimum delay to steady-state pumping and are characterized by having a semipermeable membrane wall comprising cellulose acetate butyrate ("CAB") where the CAB has a differential scanning calorimetry ("DSC") profile wherein the main or primary DSC peak has a minimum temperature peak above 228° C. and the secondary DSC peak area is equal to or less than about 30% of the total combined areas of the primary and secondary DSC peaks. CAB material exhibiting a DSC profile as described above generally has a butyryl content of less than or equal to 18.2% and generally within the range of 16.5–18.2%, an acetyl content of greater than or equal to 29.1% and generally within the range of 29.1–31.0%, and a hydroxyl content of less than or equal to 1.0%.

One presently preferred type of delivery device is a ruminal bolus, such as that disclosed and described in detail in U.S. Pat. No. 4,595,583, the entire disclosure of which is incorporated herein by reference. A ruminal bolus is a device which provides a source of medically or nutritionally useful material or other beneficial agent for a prolonged period of time. Osmotically driven ruminal boluses are placed in the rumen of a ruminant animal and retained there by means of a densifier or density element. Such boluses have an osmotic portion or expandable member which imbibes ruminal fluid through a semipermeable wall and expands, forcing a liquid or paste portion containing beneficial agent through an orifice into the rumen.

While a ruminal bolus is a presently preferred embodiment of the invention, it is to be understood that such a device is not to be construed as limiting the invention, as the delivery device designed as a dispenser can take many shapes, sizes and forms for delivering beneficial agents to a biological environment of use. Additionally, a density element or densifier is not critical to the invention, and devices according to the present invention without a density element are contemplated. Such devices are particularly suitable as implants for use with humans or animals.

The term "beneficial agent" as used herein describes any beneficial agent or compound that can be delivered by a device herein to produce a beneficial, therapeutic or useful result. The term "beneficial agent" includes medicines or drugs, such as inorganic or organic drugs, nutrients, food supplements and other agents that benefit an animal, including a warm-blooded animal, and humans. The particular agent or the amount of agent in the device is not critical to the present invention and can be any agent which gives a beneficial result present in a therapeutically effective amount (that is, an amount that gives a therapeutic or beneficial effect).

The term "exit means" as used herein comprises means suitable for the metered release of a beneficial agent formulation from the delivery device. The exit means includes at least one passageway, orifice, diffuser or the like for communicating the internal compartment of the device with the environment of use.

The following examples are merely illustrative of the present invention and they should not be construed as limiting the scope of the invention in any way, as these examples and other equivalents thereof will become more apparent to those skilled in the dispensing art in light of the present disclosure, the drawings and the accompanying claims.

EXAMPLE 1

A non-prehydrated delivery system manufactured in the shape of a dispenser adapted for the controlled delivery of ivermectin to an animal was made as follows.

First, a membrane cup in the shape of a dispenser was injection molded from a wall-forming composition comprising 50.0% cellulose acetate butyrate 171-15S (having a 29.9% butyryl content, a 17.5% acetyl content and a 0.70% hydroxyl content and having a DSC profile where the primary DSC peak has a minimum temperature peak at 245° C. and the secondary DSC peak area is 21% of the total combined areas of the primary and secondary peaks; "CAB A"); 17.3% cellulose acetate 398-10 having a 39.8% acetyl content; 21.8% Citroflex®4 tributyl citrate; 5.9% Citroflex®2 triethyl citrate; 4.0% polyethylene glycol 400; and 1.0% titanium dioxide. The final injection molded cup weighed about 12 grams.

Next, an expandable driving member designed as an osmotic tablet was manufactured in a shape that corresponds to the internal shape of the injection molded cup. The expandable driving member composition comprised 2.5 g of sodium chloride, 5.8 g of the sodium salt of polyacrylic acid polymer available as Carbopol®934P, 0.07 g of Povidone® polyvinyl pyrrolidone, and 0.10 g of magnesium stearate. The composition was compressed under 10 tons into an osmotic expansion tablet, 0.850 inches in diameter, 0.66 inches in height, and having a tablet density of approximately 1.56 g/cc.

Next, 880 g of ivermectin was added with high shear mixing at 90° C. to 3040 g of microcrystalline food grade wax, having a melting point of 150°–160° F. and a Kinematic viscosity at 99° C. of 7.3–12.6 centistokes, and 80 g of silicon dioxide.

Next, 490 g of food grade microcrystalline wax, as described in the paragraph immediately above, was added to 490 g of a food grade microcrystalline wax having a 180°–190° F. melting point and a Kinematic viscosity at 99° C. of 14.3–18.0 centistokes, and the mixture was heated to 90° C. Then, 20 g of silicon dioxide was added to the molten waxes and the mixture was blended to give the partition layer formulation.

The dispenser was assembled by first placing the osmotic expansion tablet into the membrane cup. Next, 4.2 g of the partition layer formulation was added to the membrane cup in contacting relation with the osmotic expansion tablet. After the partition layer was cooled, 7.8 g of the formulation comprising the ivermectin was added to the membrane cup, followed by cooling the cup. Then, a density element comprising iron with a central bore and dimensioned to conform to the inside of the membrane cup was placed into the cup. The density element was inserted into the membrane cup until the bottom of the density element contacted the thermo-responsive ivermectin formulation. An exit member made from nylon polymer as a grid, with a plurality of openings of approximately 18 mesh was placed in the exit bore of the density element.

Next, the membrane cup was rotated in front of a hot air gun until the tip of the membrane softened and became thermoplastic. The membrane cup next was placed into a crimping fixture pressurized with compressed air, followed by a crimping head activated, positioned and rotated on top of the membrane cup to close over the edges of the exit member to yield the dispenser.

In like manner, a delivery device having a membrane cup having the above formulation except that it comprised cellulose acetate butyrate 171-15S having a 29.3% butyryl content, a 17.6% acetyl content and a 1.2% hydroxyl content and a primary DSC peak having a minimum temperature peak at 226° C. and a secondary DSC peak area of 42% ("CAB E") rather than CAB A was prepared.

In the same way, a delivery device having a membrane cup having the above formulation except that it comprised cellulose acetate butyrate 171-15S having a 29.7% butyryl content, a 17.0% acetyl content and a 0.96% hydroxyl content and a primary DSC peak having a minimum temperature peak at 229° C. and a secondary DSC peak area of 21% ("CAB Z") rather than CAB A was prepared.

Delivery devices prepared as above were tested for their time and consistency of startup by placing the devices in deionized water at 40° C. At intervals, each device was removed to new water, and the ivermectin formulation that had extruded through the orifice was collected, dried and weighed gravimetrically to determine the amount of formulation released.

Figure 4:
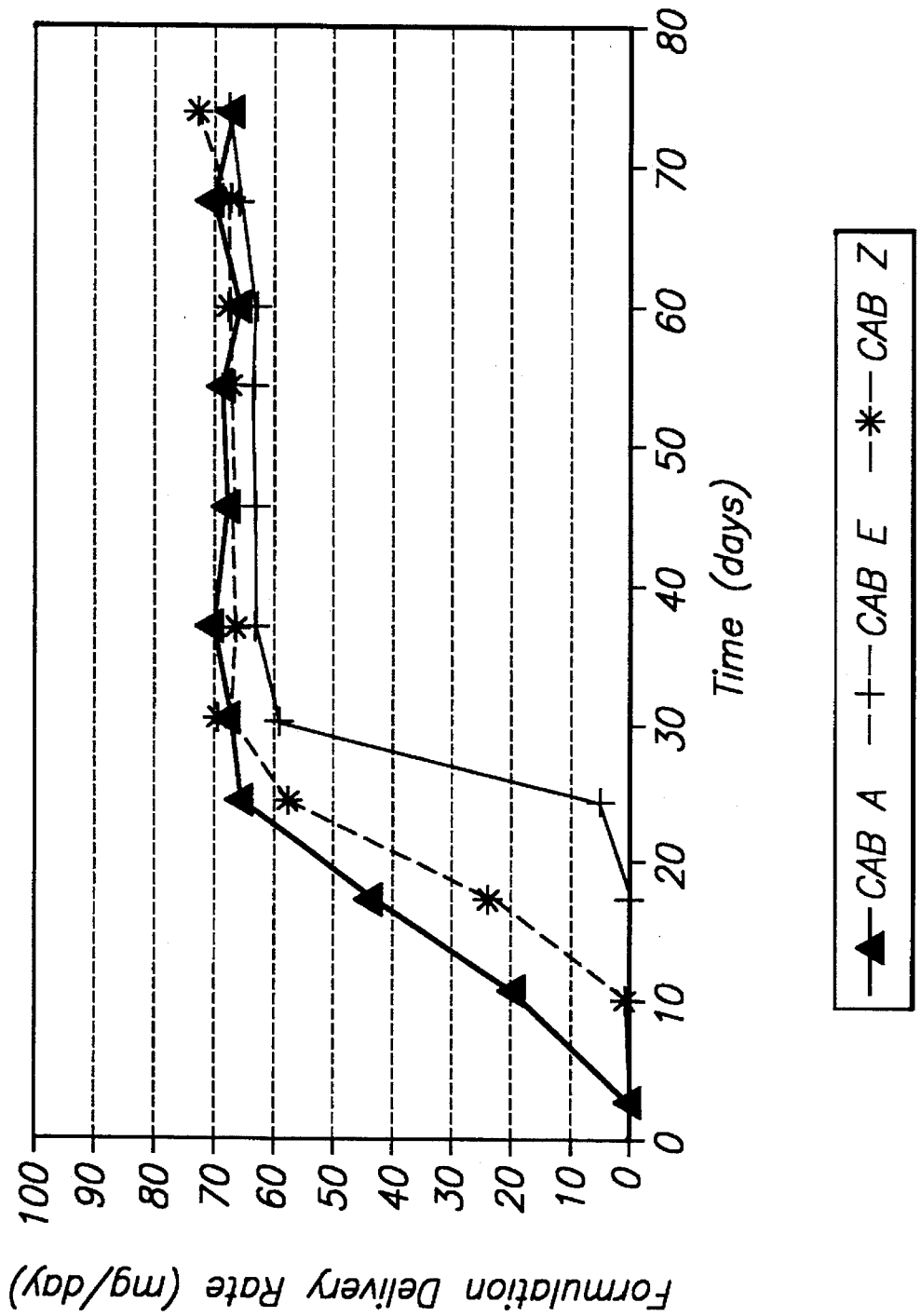
FIG. 4 is a graph presenting the average in vitro release rates over 70 days for anhydrous (not prehydrated) osmotic delivery devices having a semipermeable membrane comprising CAB A, CAB E, or CAB Z.

Accompanying FIG. 4 depicts the in vitro release rate profiles for ivermectin from dispensers made according to this example.

EXAMPLE 2

A prehydrated delivery device according to the present invention for the controlled delivery of the beneficial drug ivermectin with rapid startup was made following the procedures of Example 1 (the device having a membrane cup comprising CAB Z), except as follows: After assembly, the delivery device of Example 1 (with CAB Z) was prehydrated by storing the system, packaged together with 1.3 mL of water, at room temperature for 60 days. This device was then tested for its time and consistency of startup, following the procedures of Example 1.

Figure 5:
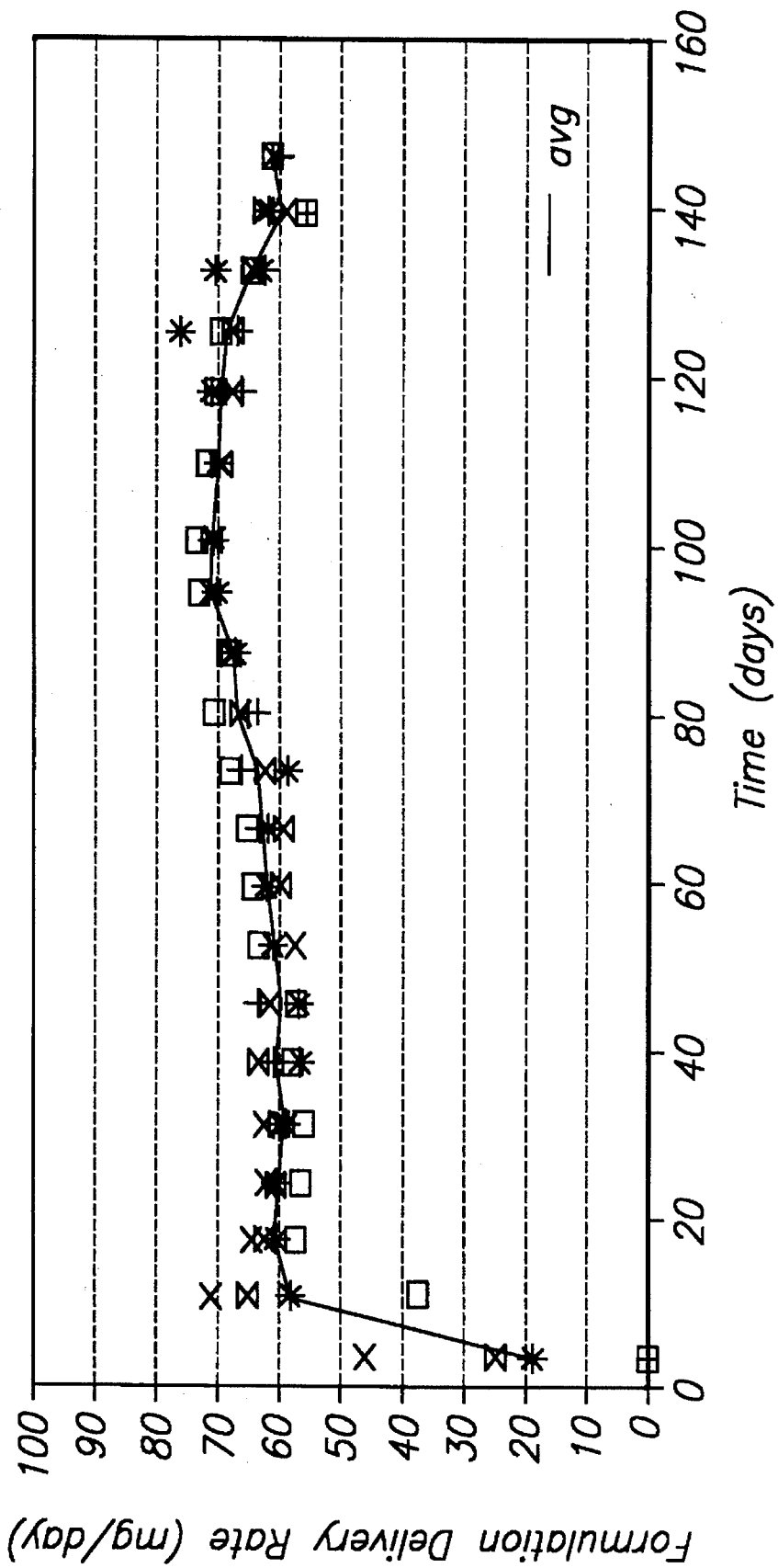
FIG. 5 is a graph presenting the average in vitro release rate over 140 days for prehydrated osmotic delivery devices having a semipermeable membrane comprising CAB Z.

FIG. 5 depicts the in vitro release rate for a delivery device made according to this procedure.

What is claimed is:

1. A process for selecting cellulose acetate butyrate for use in an osmotic delivery device, wherein the process comprises:
   1) generating differential scanning calorimetry ("DSC") profiles for representative samples from lots of cellulose acetate butyrate ("CAB") being considered for use in the osmotic delivery device, said profiles having primary and secondary DSC minimum temperature peaks and 2) selecting for use in the manufacture of said osmotic delivery devices those lots of CAB for which the samples exhibit an acceptable DSC profile, which, if analyzed on a Du Pont 2100 Thermal Analyzer set to equilibrate the sample at a temperature of 30° C., and heat the sample to 270° C. at 20° C. per minute, would exhibit a DSC profile wherein the profile has a minimum temperature peak above 228° C. and an area under the secondary minimum temperature peak which is equal to or less than 30% of the total combined areas under the primary and secondary DSC peaks.

2. The process of claim 1, further including 1) determining the butyryl, acetyl and hydroxyl content of the cellulose acetate butyrate; and 2) selecting for use in the osmotic delivery device those lots of the cellulose acetate butyrate that have a butyryl content of between 16.5% and 18.2%, an acetyl content between 29.1% and 31.0% and a hyroxyl content that is less than or equal to 1.0%.

3. A process according to claim 2 wherein the cellulose acetate butyrate has a hydroxyl content of between 0.55% and 0.95%.

4. A process for making an improved semi-permeable membrane component formed from cellulose acetate butyrate, said process comprising:

1) generating DSC profiles for representative samples from lots of cellulose acetate butyrate ("CAB") being considered for use in the device, said profiles having a primary and secondary minimum temperature peaks; and 2) forming said membrane component from those lots of CAB for which the samples exhibit an acceptable DSC profile, which, if tested on a Du Pont Thermal Analyzer 2100 set to equilibrate the sample at a temperature of 30° C. and heat the sample to 270° C. at 20° C. per minute, would exhibit a DSC profile wherein the profile has a minimum temperature peak above 228° C. and an area under the secondary peak which is equal to or less than 30% of the total combined areas under the primary and secondary minimum temperature peaks.

5. A process for making an osmotic delivery device having acceptable start-up characteristics and comprising a semipermeable membrane component formed from cellulose acetate butyrate, said process comprising:

1) generating DSC profiles for representative samples from lots of the cellulose acetate butyrate ("CAB") being considered for use in the device, said profiles having a primary and secondary minimum temperature peaks; and 2) forming said membrane component from those lots of CAB for which the samples exhibit an acceptable DSC profile, which, if tested on a Du Pont Thermal Analyzer 2100 set to equilibrate the sample 30° C. and heat the sample to 270° C. at 20° C. per minute, would exhibit a DSC profile wherein the profile has a minimum temperature peak above 228 C. and an area under the secondary minimum temperature peak which is equal to or less than 30% of the total combined areas under the primary and secondary peak.

6. A process for selecting CAB for use in the manufacture of osmotic delivery devices having acceptable start-up characteristics comprising:

a) determining endothermic properties for representative samples from lots of CAB being considered for use in the device; and b) selecting for use in the device those lots of CAB for which the endothermic properties of the samples correspond to the endothermic properties of CAB known to produce acceptable start-up characteristics.

7. A process for manufacturing an osmotic delivery device having acceptable start-up characteristics and comprising a semipermeable membrane component formed from cellulose acetate butyrate ("CAB"), said process comprising:

a) determining endothermic properties for representative samples from lots of CAB being considered for use in the device; and b) forming said membrane component from those lots of CAB for which the endothermic properties of the samples correspond to the endothermic properties of CAB known to produce acceptable start-up characteristics.

8. A process according to claim 7 wherein the cellulose acetate butyrate has a hydroxyl content of between 0.55% and 0.95%.

* * * * *